United States Patent
Park

(10) Patent No.: US 10,512,585 B2
(45) Date of Patent: Dec. 24, 2019

(54) DEVICE FOR EXERCISING MUSCLES IN EYES

(71) Applicant: Sung-yong Park, Busan (KR)

(72) Inventor: Sung-yong Park, Busan (KR)

( * ) Notice: Subject to any disclaimer, the term of this patent is extended or adjusted under 35 U.S.C. 154(b) by 548 days.

(21) Appl. No.: 15/281,530

(22) Filed: Sep. 30, 2016

(65) Prior Publication Data

US 2018/0092796 A1   Apr. 5, 2018

(51) Int. Cl.
*A61H 5/00* (2006.01)
*A61B 3/00* (2006.01)
*A61B 3/09* (2006.01)
*G02B 7/02* (2006.01)

(52) U.S. Cl.
CPC .............. *A61H 5/00* (2013.01); *A61B 3/00* (2013.01); *A61B 3/09* (2013.01); *G02B 7/02* (2013.01); *A61H 2201/1215* (2013.01); *A61H 2201/165* (2013.01); *A61H 2201/1666* (2013.01); *A61H 2201/501* (2013.01); *A61H 2201/5005* (2013.01); *A61H 2201/5043* (2013.01); *A61H 2205/024* (2013.01)

(58) Field of Classification Search
CPC .............. A61H 5/00; A61H 2201/12; A61H 2201/1207; A61H 2201/123; A61H 2201/15; A61H 2201/5023; A61H 2201/5043; A61H 2201/5046; A61H 2201/0157; A61H 2201/1215; A61H 2201/1481; A61H 2201/149; A61H 2205/024; A61B 3/00; A61B 3/024; A61B 3/14; A61B 3/0091; A61B 3/0032; A61B 3/0041; G02B 7/02

See application file for complete search history.

(56) References Cited

U.S. PATENT DOCUMENTS

| | | | | | |
|---|---|---|---|---|---|
| 4,408,846 | A | * | 10/1983 | Balliet | A61H 5/00 351/203 |
| 4,778,268 | A | * | 10/1988 | Randle | A61B 3/09 351/203 |
| 4,838,677 | A | * | 6/1989 | Bronskill | A61H 5/00 351/203 |

(Continued)

FOREIGN PATENT DOCUMENTS

| JP | H08206166 A | 8/1996 |
|---|---|---|
| JP | H08257078 A | 10/1996 |

(Continued)

OTHER PUBLICATIONS

An International Search Report and Written Opinion issued by the International Searching Authority dated Jul. 31, 2017 in connection with international patent application No. PCT/KR2016/014735.

(Continued)

*Primary Examiner* — Michael J Tsai
*Assistant Examiner* — Matthew R Moon
(74) *Attorney, Agent, or Firm* — Baker & McKenzie

(57) ABSTRACT

A device for exercising muscles in eyes, the device including: a housing which is formed with an ocular hole corresponding to a user's eye; a display which displays a target image in front of a user' eyes in an eye line; a lens which is arranged in between the ocular hole and the display; and a lens driver which drives the lens to move forward and backward along the eye line.

15 Claims, 4 Drawing Sheets

(56) References Cited

U.S. PATENT DOCUMENTS

| | | | |
|---|---|---|---|
| 5,596,378 A | 1/1997 | Kelman | |
| 2006/0103808 A1 | 5/2006 | Horie | |
| 2007/0038142 A1 | 2/2007 | Todd et al. | |
| 2009/0168016 A1* | 7/2009 | Ohkawa | A61H 5/00 351/203 |
| 2010/0118272 A1* | 5/2010 | Iwasaki | A61B 3/09 351/239 |
| 2012/0069296 A1 | 3/2012 | Li et al. | |
| 2017/0296421 A1* | 10/2017 | Travers | A61B 3/032 |
| 2018/0032103 A1* | 2/2018 | Eskilsson | G06F 1/163 |
| 2018/0263488 A1* | 9/2018 | Pamplona | A61B 3/09 |

FOREIGN PATENT DOCUMENTS

| | | |
|---|---|---|
| JP | H0956764 A | 3/1997 |
| JP | H10314211 A | 12/1998 |
| JP | 2004351103 A | 12/2004 |
| JP | 2009153658 A | 7/2009 |
| JP | 2010088539 A | 4/2010 |
| JP | 2010148738 A | 7/2010 |
| JP | 2014038302 A | 2/2014 |
| KR | 100526023 B1 | 11/2005 |
| KR | 101370588 B1 | 3/2014 |
| KR | 101408237 B1 | 6/2014 |
| KR | 101663765 B1 | 10/2016 |

OTHER PUBLICATIONS

An International Search Report and Written Opinion issued by the International Searching Authority dated Jul. 28, 2017 in connection with international patent application No. PCT/KR2016/014645.

An International Preliminary Report on Patentability Chapter I issued by the International Bureau of WIPO dated Apr. 2, 2019 in connection with international patent application No. PCT/KR2017/011094.

* cited by examiner

DEVICE FOR EXERCISING MUSCLES IN EYES

FIELD OF THE INVENTION

Apparatuses and methods consistent with the exemplary embodiments relate to a device for exercising muscles in eyes.

BACKGROUND OF THE INVENTION

Ocular muscles related to a human's eyesight include ciliary muscles, rectus, iris muscles, etc. The eyesight may be protected or recovered by exercising such ocular muscles. In particular, the eyesight is closely related to the ciliary muscles. Here, the ciliary muscles are involuntary muscles that are not controlled by individual volition. However, when a focal distance of a lens in front of eyes is changed, the ciliary muscles unconsciously act in response to this change. Based on such characteristics of the ciliary muscles, there has been widespread a method of using a flipper to change the focal distance of the lens and thus improve the reactivity and strength of the ciliary muscles, thereby recovering the eyesight.

Such an exercising method using the flipper is inconvenient for a user since s/he has to repetitively and personally rotate the flipper at predetermined intervals.

To solve this inconvenience of using the flipper, there have been proposed many eyesight exercise devices for automatically changing the focal distance of the lens. However, these eyesight exercise devices have to include a plurality of lenses different in a diopter value from one another and thus have complicated inner structures. Besides, if the eyesight exercise device is used by a plurality of users who are different in eyesight from each other, they have to prepare separate eyepieces suitable for their own eyesight or use the eyesight exercise device while wearing glasses. Accordingly, it is difficult to generally use such a conventional eyesight exercise device.

SUMMARY OF THE INVENTION

Accordingly, an aspect of one or more exemplary embodiments may provide a device for exercising muscles in eyes, which can have a simple structure and be generally used for users who are different in eyesight.

Another aspect of one or more exemplary embodiments may provide a device for exercising muscles in eyes, which can provide eyesight exercise customized for a user as s/he freely selects an exercise mode or an exercise condition in accordance with his/her preference or will.

The foregoing and other aspects of an exemplary embodiment are achieved by providing a device for exercising muscles in eyes, the device including: a housing which is formed with an ocular hole corresponding to a user's eye; a display which displays a target image in front of a user' eyes in an eye line; a lens which is arranged in between the ocular hole and the display; and a lens driver which drives the lens to move forward and backward along the eye line.

Here, the device for exercising muscles in eyes may further include a controller which sets at least one exercise region previously set within a full movable range of the lens, and controls the lens driver to drive the lens to reciprocate within the exercise region. In this case, the exercise region may be automatically set and the lens may be automatically moved, thereby improving a user's convenience with precise exercise.

Further, the controller may set a predetermined emmetropia region within the movable range, and the exercise region may include an extra region that goes beyond one of a close limit and a remote limit of the emmetropia region. Therefore, a user can set the exercise condition desired and preferred by him/her.

In addition, the device for exercising muscles in eyes may further include a user input portion which receives a user's input, wherein at least one of the emmetropia region and the exercise region is set based on the user's input.

BRIEF DESCRIPTION OF THE DRAWINGS

The above and/or the aspects will become apparent and more readily appreciated from the following description of exemplary embodiments, taken in conjunction with the accompanying drawings, in which.

DETAILED DESCRIPTION OF THE INVENTION

Below, a device for exercising muscles in eyes according to exemplary embodiments will be described in detail with reference to accompanying drawings.

Figure 1:
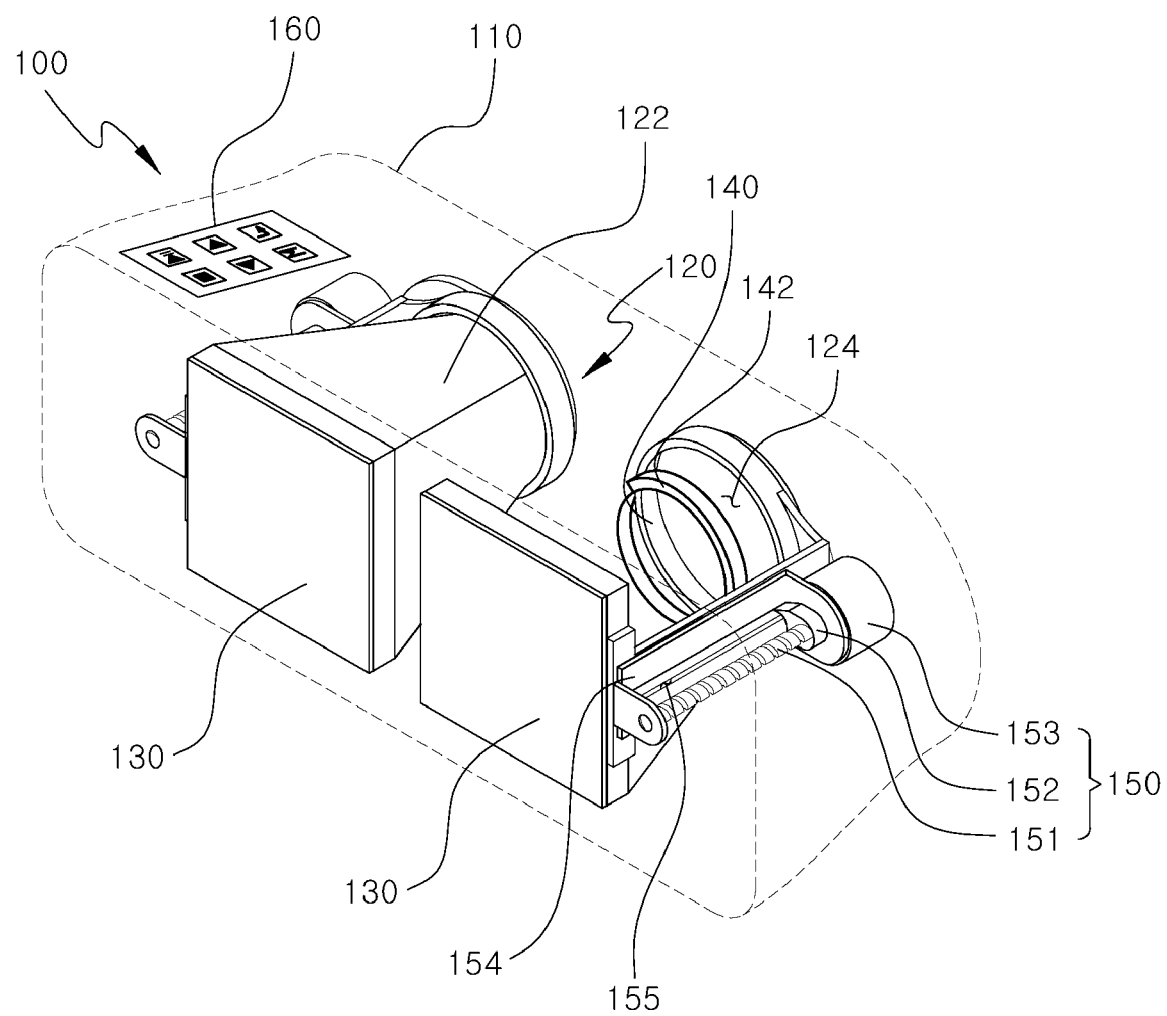
FIG. 1 is a perspective view of a device for exercising muscles in eyes according to an exemplary embodiment.

FIG. 1 is a perspective view of a device for exercising muscles in eyes according to an exemplary embodiment. In this embodiment, the device for exercising muscles in eyes include a pair of eyesight exercise units 120 arranged left and right inside a housing 110 shown in a dotted line. Each exercise unit 120 includes a unit casing 122. FIG. 1 illustrates that the unit casing 122 is removed from one of the two units 120 so as to show an inner structure thereof.

The unit casing 122 includes an ocular hole 124 and a display 130 arranged to face each other along an eye line. The display 130 displays a target image for eyesight exercise. The ocular hole 124 is closest to a user's eye when s/he looks the target image displayed on the display 130 therethrough.

Further, a lens 140 is arranged in between the ocular hole 124 and the display 130. The lens 140 is held by a lens holder 142, and the lens holder 142 is coupled to a lead screw 151 by a moving body 152. The lead screw 151 is rotated by a driving motor 153, and this rotation makes the lens holder 142 and the lens 140 coupled to the lens holder 142 linearly slide between the ocular hole 124 and the display 130. To this end, a fastening supporter 154 fastened to the unit casing 122 is formed with a guide slot 155 extended along the eye line and guiding the lens holder 142 to slide.

On the top of the housing 110, a user input portion 160 is provided to receive a user's input. Through the user input portion 160, a user may input necessary information or sets an exercise condition, an exercise mode, etc.

Further, the housing 110 may be provided with a strap (not shown) or a temple (not shown) to be worn on a user's face.

The housing 110 approximately has a box shape, and has a rear side rounded/freeformed corresponding to a user's facial profile so as to give comfortable fit when s/he wears the device. Further, the rear side of the housing 110 is opened corresponding to the ocular holes 124 so that a user can look the target image displayed inside the housing 110 through the ocular hole 124.

The display 130 displays a target image in front of a user's eyes. The target image displayed on the display 130 may include a still image such as a landscape photograph, a figure, a dot, a geometric pattern, etc. or a moving image. To display such an image, the display 130 may be achieved by an electronic display device such as a liquid crystal display (LCD), an organic light emitting diode (OLED), etc.

On the contrary, the display 130 may be achieved by a simple slide where a predetermined target image is invariably displayed. In this case, the display 130 may be fastened to a proper mounting structure provided in the housing 110, or replaceably mounted to a sliding groove or the like structure.

The lens 140 is mounted to the lens holder 142 and movably arranged in between the ocular hole 124 and the target image. A user looks the target image positioned in front of his/her eyes through the ocular hole 124 and the lens 140. In this embodiment, the lens 140 is achieved by a convex lens, but not limited thereto. Alternatively, the lens 140 may be achieved by a concave lens, a polarization lens, an Omni-focal lens, a color lens, or the like various lenses. The lens 140 changes a focus between a user's eye and the target image whole moving along a user's eye line.

A lens driver 150 drives the lens 140 to move forward and backward along a user's eye line. The lens driver 150 includes the lead screw 151, the moving body 152 movably coupled to the lead screw 151, and a driving motor 153 for driving the lead screw 151 to rotate.

The lead screw 151 is rotatably coupled to the fastening supporter 154.

The moving body 152 is movably coupled to the lead screw 151 and moves the lens 140 forward and backward along a user's eye line as the lead screw 151 rotates. The moving body 152 is connected to the lens holder 142 via a slit-shaped guide hole 155 elongated along the moving direction of the lens 140. Therefore, if the lead screw 151 rotates, the moving body 152 moves forward and backward while being guided by the guide hole 155.

The driving motor 153 is fastened to the fastening supporter 154. The driving motor 153 has a driving shaft connecting with the lead screw 151 and drives the lead screw 151 to rotate.

The exercise unit 120 in between the ocular hole 124 and the display 130 is separated from the other spaces and closed by the unit casing 122. By the unit casing 122, a user can look only the target image displayed by the display 130 corresponding to each of eyes. The unit casing 122 may be shaped like not only a cylinder but also a partition for separating the housing 110 into left and right sections.

Figure 2:
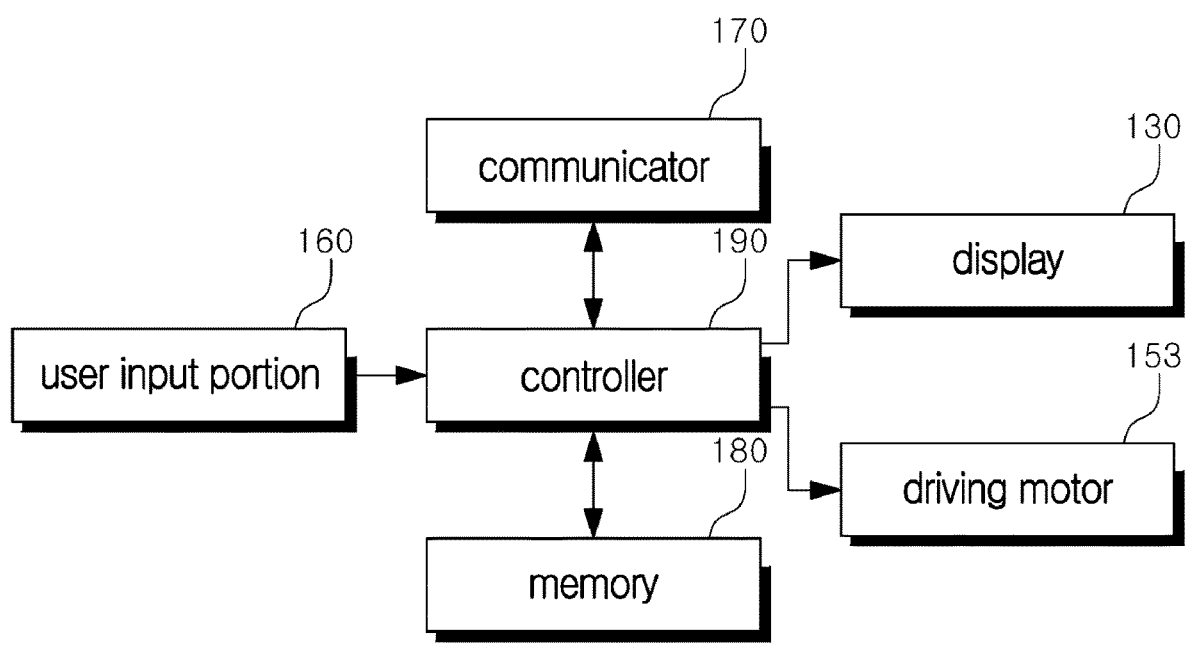
FIG. 2 is a control block diagram of a device for exercising muscles in eyes according to an exemplary embodiment.

FIG. 2 is a control block diagram of a device for exercising muscles in eyes according to an exemplary embodiment.

The user input portion 160 is provided on the top or lateral side of the device 100 for exercising muscles in eyes, and the controller 190 receives information or conditions input by a user through the user input portion 160. The user input portion 160 may be achieved by a keypad, a touch screen, a microphone, etc.

A communicator 170 communicates with a smart phone, a tablet computer, a user server, or the like external device by a wire or wirelessly. Through the communicator 170, the device 100 for exercising muscles in eyes may transmit data to the external device or receive data from the external device.

A memory 180 stores various pieces of data needed for operating the device 100 for exercising muscles in eyes, such as user information, eyesight data, exercise data, etc. Under control of the controller 190, the memory 180 transmits the stored data to the controller 190, the communicator 170 or the like, or stores the received data therein.

The controller 190 controls general operations of the device 100 for exercising muscles in eyes according to an exemplary embodiment. The controller 190 may be achieved by a microcontroller unit (MCU), a central processing unit (CPU), an application processor (AP), etc.

The controller 190 may control a pair of displays 130 independently. Thus, the device 100 for exercising muscles in eyes according to an exemplary embodiment can be applied to eyesight exercise for a left eye, a right eye or both eyes. The controller 190 controls operations of the driving motor 153 and controls sliding movement of the lens 140.

The foregoing device 100 for exercising muscles in eyes may be driven using power from a built-in battery (not shown) or from a connected external power source.

In the foregoing exemplary embodiment, the lens driver 150 employs the driving motor 153 for rotation, but not limited thereto. Alternatively, the lens driver 150 may be achieved in such a manner that a user personally rotates a dial connected to the lens 140. Besides, the lens driver 150 may be achieved variously as long as it can move the lens 140 forward and backward within the housing 110.

In the foregoing device 100 for exercising muscles in eyes, the lens 140 is moved to change the focal distance between the target image and the eyes, thereby strengthening ciliary muscles related to the eyesight. Further, only one pair of lens is enough to strengthen a user's ocular muscles, thereby providing the device 100 for exercising muscles in eyes.

Figure 3:
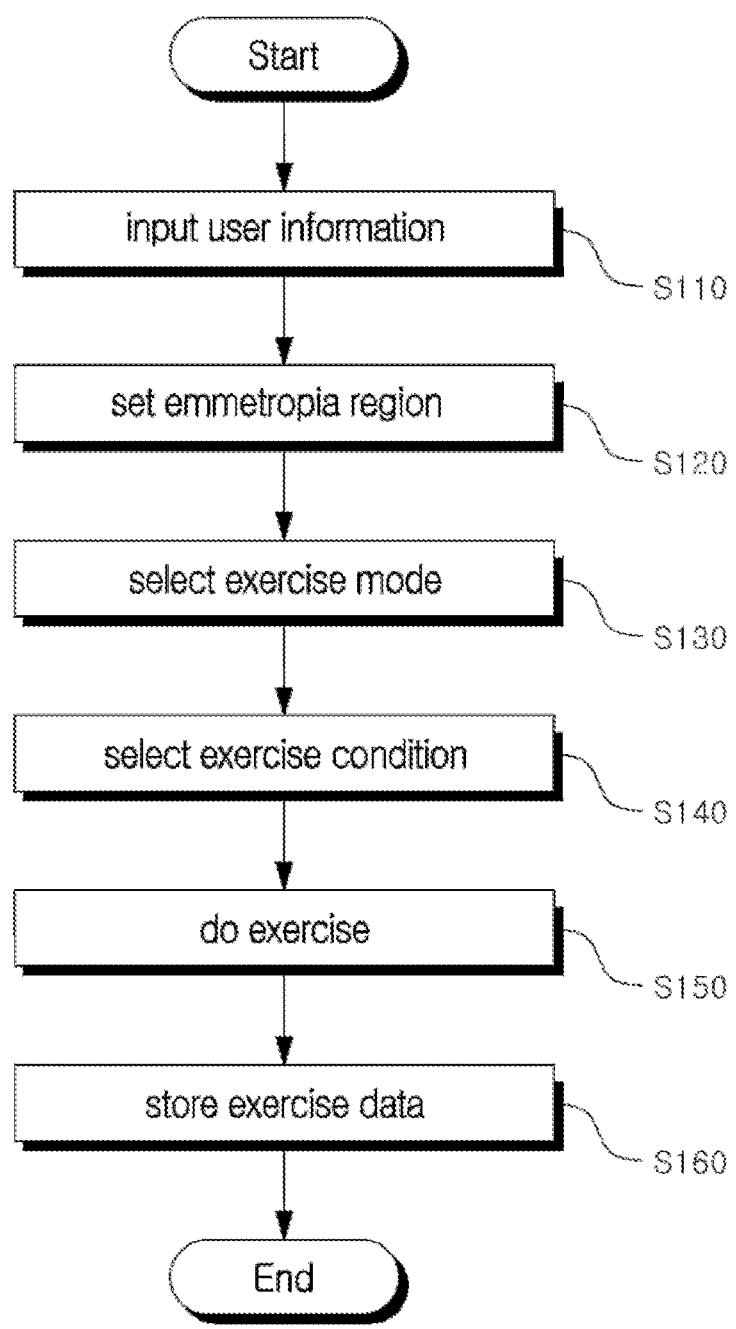
FIG. 3 is a flowchart for explaining a process of exercising muscles in eyes according to an exemplary embodiment.
Figure 4:
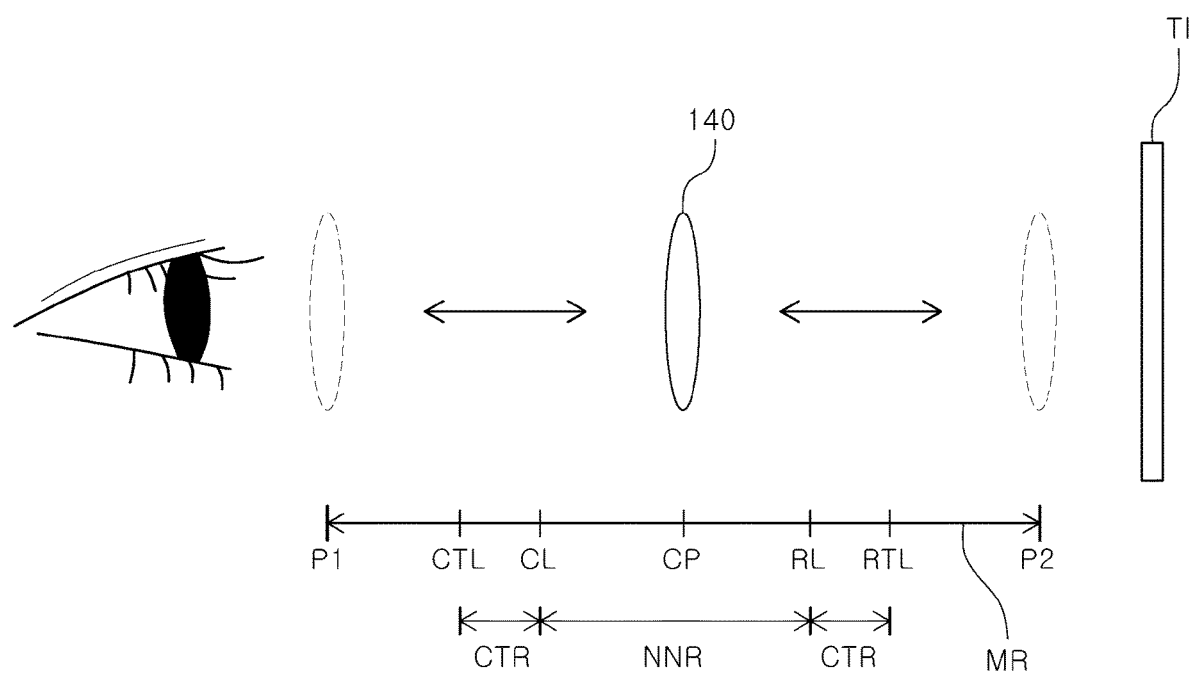
FIG. 4 is a view for explaining the process of exercising muscles in eyes according to an exemplary embodiment.

FIG. 3 is a flowchart for explaining a process of exercising muscles in eyes according to an exemplary embodiment, and FIG. 4 is a view for explaining the process of exercising muscles in eyes according to an exemplary embodiment. Below, the eyesight exercise using the device 100 for exercising muscles in eyes according to an exemplary embodiment will be described with reference to FIG. 3 and FIG. 4.

First, user information is input to the device 100 for exercising muscles in eyes (S110).

The user information may include a user's name, a user's age, a user's eyesight information. The user information may be received from the external device through the communicator 170 or may be personally input by a user through the user input portion 160. Based on the received user information, the controller 190 may generate libraries according to users, and store them in the memory 180.

Next, an emmetropia region is set (S120).

The emmetropia region NNR refers to a predetermined movable range of the lens 140, in which a user can recognize the target image. The emmetropia region NNR may be automatically set by the controller 190 based on received user information about eyesight, or may be personally set by a user through the user input portion 160.

If the controller 190 automatically sets the emmetropia region NNR, the controller 190 sets an eyesight center position CP of the lens corresponding to an eyesight value input by a user. The controller 190 determines a close limit CL and a remote limit RL, which are spaced apart by a set distance from the set eyesight center position CP of the lens in forward and backward directions, and sets the determined region between the close limit CL and the remote limit RL as the emmetropia region NNR. The width of the emmetropia region NNR set by the controller 190 may be varied depending on users' ages.

Further, the foregoing emmetropia region NNR may be personally set by a user through the device 100 for exercising muscles in eyes according to an exemplary embodiment. In this case, a user wears the device 100 for exercising muscles in eyes, and starts an operation for setting the emmetropia region. If a command for setting the emmetropia region is issued, the controller 190 controls the display 130 to display a predetermined target image, and controls the lens driver 150 to move the lens 140 to a predetermined position, e.g. a moving remote limit P2 or a moving close limit P1 within the whole movable range MR. In the state that the lens 140 is positioned at the moving remote limit P2 or the moving close limit P1, the lens 140 typically goes beyond a user's emmetropia region and therefore a user cannot clearly recognize a target image TI. As the controller 190 gradually moves the lens 140 from the moving remote limit P2 or the moving close limit P1 to the moving close limit P1 or the moving remote limit P2, a user more clearly recognizes the target image TI.

At a point of time when the target image TI is relatively clearly recognized, a user inputs a first user input through the user input portion 160. The lens 140 continues to move toward the moving close limit P1 or the moving remote limit P2, and a user inputs a second user input through the user input portion 160 at a point of time when the clearly recognized target image TI becomes blur. The controller 190 sets the remote limit RL or the close limit CL by the position of the lens 140 at the point of time when the first user input is input, sets the close limit CL or the remote limit RL by the position of the lens 140 at the point of time when the second user input is input, and sets the emmetropia region NNR by a region in between the remote limit RL and the close limit CL.

If the lens 140 is positioned within the emmetropia region NNR, a user can clearly recognize the target image TI through the lens 140. To determine the emmetropia region NNR more reliably, a user may repeat the foregoing processes and calculate an average of results from the foregoing processes to thereby determine the emmetropia region NNR.

A user may select the exercise mode. The exercise mode may include a regional exercise mode for exercise within the emmetropia region NNR, an extra-regional exercise mode for exercise out of the emmetropia region NNR, an intersection exercise mode for exercise within and out of the emmetropia region NNR, an intensive exercise mode for exercise in a predetermined region within or out of the emmetropia region NNR, etc.

Thus, a user may do the eyesight exercise by selecting his/her favorite exercise mode among the foregoing exercise modes. Such exercise modes may be personally selected by a user, but not limited thereto. Alternatively, the exercise modes may be automatically selected by the controller 190.

If a user selects the intensive exercise mode, an intensive exercise region CTR may be automatically set by the controller 190 or personally set by a user.

If the controller 190 automatically sets the intensive exercise region CTR, the controller 190 first determines a close exercise limit CTL or a remote exercise limit RTL spaced apart by a preset distance from the close limit CL or the remote limit RL. At this time, the distance spaced to determine the close exercise limit CTL or the remote exercise limit RTL may be varied depending on users' ages. The controller 190 may set the intensive exercise region CTR by a range between the close limit CL and the close exercise limit CTL or by a range between the remote limit RL and the remote exercise limit RTL.

If a user personally sets the intensive exercise region CTR, the intensive exercise region CTR is set as follows.

A user wears the device 100 for exercising muscles in eyes, and begins an operation for setting the intensive exercise region. If a command for setting the intensive exercise region is issued, the controller 190 controls the display 130 to display a predetermined target image TI, and controls the lens driver 150 to move the lens 140 to one of the close limit CL or the remote limit RL. For convenience of description, suppose that the lens 140 is moved to the close limit CL.

The controller 190 controls the lens driver 150 to repeat a measuring operation. The measuring operation is an operation moving the lens 140 from the close limit CL toward the moving close limit P1 by a preset spacing distance and keeping that position for a preset standby time.

If the target image TI recognized through the lens 140 does not become clear even after the preset standby time elapses, a user inputs a predetermined signal through the user input portion 160. If receiving a predetermined signal through the user input portion 160, the controller 190 stops the measuring operation and sets the close exercise limit CTL by the position of the lens 140 at the point of time when the signal is received.

The foregoing spacing distance set for determining the intensive exercise region CTR may be varied depending on the width of the previously determined emmetropia region NNR, and may be for example set to increase as the width of the emmetropia region NNR becomes larger. Further, the standby time set for determining the intensive exercise region CTR may be varied depending on users' ages, and may be for example set to increase as the users' ages become higher.

The determined intensive exercise region CTR refers to a region of reflecting a range of an accommodation force reserve that a user's eyes have. By intensively performing the eyesight exercise within this intensive exercise region CTR, a user's eyesight is more effectively improved.

After the exercise mode is selected, the exercise condition is set (S140).

The exercise condition includes the kind of target images, a method of moving the lens 140, a distance of moving the lens 140, time taken from spacing to stopping the lens 140, etc.

Among the various kinds of target images TI as described above, one target image is selected by a user or automatically selected by the controller 190.

The method of moving the lens 140 is selected by a user or automatically selected by the controller 190. As the method of moving the lens 140, one of an intermittent moving method and a continuous moving method may be selected.

The distance of spacing the lens 140 and the time taken from spacing to stopping the lens 140 are selected by a user or automatically selected by the controller 190.

If the exercise conditions are completely set, the exercise is launched (S150).

The device 100 for exercising muscles in eyes performs exercise operations in accordance with the set exercise mode and exercise condition. The device 100 for exercising muscles in eyes repetitively performs moving the lens 140 by a preset spacing distance within the set exercise region and then being on standby for a preset standby time. A user's ciliary muscles contracts and relax to be adapted for change in the focal distance between the lens 140 and the target image TI as the lens 140 moves. If this exercise operation is repeated, the ciliary muscle is strengthened as it is continuously contracted and relaxed.

When the set exercise operation is completed, the device 100 for exercising muscles in eyes terminates the exercise operation and stores exercise data in the memory 180 (S160).

The exercise data includes information about how long it takes to terminate one cycle of the exercise, what exercise mode, and what exercise condition. The exercise data is stored according to respective users, and the stored exercise data may be analyzed to check improvement in a user's eyesight due to the exercise. Thus, a user checks how much his/her eyesight has improved, and effectively makes the following exercise plan and direction.

In the foregoing device 100 for exercising muscles in eye, the exercise mode and the exercise condition are automatically determined in accordance with a user's eyesight so as to perform the eyesight exercise, and it is thus convenient for a user to do the eyesight exercise.

Further, a user can personally determine the emmetropia region NNR or the intensive exercise region CTR. Using the determined emmetropia region NNR, a user can set an exercise range or do the exercise within the intensive exercise region, thereby more effectively improving his/her eyesight.

In addition, the device 100 for exercising muscles in eyes according to an exemplary embodiment may exercise the left eye or the right eye independently or both the left and right eyes.

Further, the device 100 for exercising muscles in eyes according to an exemplary embodiment can be used for both near-sighted exercise and far-sighted exercise.

As described above, there is provided a device for exercising muscles in eyes, which can have a simple structure and be generally used for users who are different in eyesight.

Further, according to an exemplary embodiment, there is provided a device for exercising muscles in eyes, which can provide eyesight exercise customized for a user as s/he freely selects an exercise mode or an exercise condition in accordance with his/her preference or will.

Although a few exemplary embodiments have been shown and described, it will be appreciated by those skilled in the art that changes may be made in these exemplary embodiments without departing from the principles and spirit of the invention, the scope of which is defined in the appended claims and their equivalents.

What is claimed is:

1. A device for exercising muscles in eyes, comprising:
a housing having an ocular hole corresponding to a user's eye, a line of sight being defined to intersect with the ocular hole;
a target image disposed on the line of sight;
a lens disposed on the line of sight and between the ocular hole and the target image;
a lens driver configured to drive the lens to move forward and backward along the line of sight; and
a controller configured to
determine an emmetropia region,
set an exercise region that includes a region beyond at least one of a close limit and a remote limit of the emmetropia region, and
control the lens driver to drive the lens to reciprocate in the region of the exercise region beyond at least one of the close limit and the remote limit of the emmetropia region.

2. The device according to claim 1, wherein the controller is configured to set the exercise region within a full movable range of the lens, and control the lens driver to drive the lens to reciprocate within the exercise region.

3. The device according to claim 2, wherein the controller is configured to set the emmetropia region as a predetermined emmetropia region within the movable range, and the exercise region includes the predetermined emmetropia region and the region beyond at least one of the close limit and the remote limit of the emmetropia region.

4. The device according to claim 3, further comprising a user input device configured to receive a user's input, wherein
the controller is configured to set at least one of the emmetropia region and the exercise region based on the user's input.

5. The device according to claim 4, wherein the controller is configured to
control the lens driver to drive the lens proximal a limit of the full moveable range of the lens,
control the lens driver to drive the lens towards an opposite limit of the full moveable range of the lens,
receive a first user input from the user input device indicating that the target image is recognized,
continue to control the lens driver to drive the lens towards the opposite limit,
receive a second user input from the user input device indicating that the target image is blurry, and
determine the emmetropia region based on the first user input and the second user input.

6. The device according to claim 4, wherein the controller is configured to
control the lens driver to drive the lens to a position outside of the emmetropia region,
wait for a standby time period,
receive a user input from the user input device indicating that the target image did not become clear, and
set the region beyond at least one of the close limit and the remote limit of the emmetropia region based on a location of the lens outside of the emmetropia region.

7. The device according to claim 1, further comprising a display configured to display the target image.

8. The device according to claim 1, wherein the controller is configured to set the exercise region to include a region beyond the close limit and a region beyond the remote limit of the emmetropia region.

9. The device according to claim 1, wherein the controller is configured to set the region beyond at least one of the close limit and the remote limit of the emmetropia region based on an age of the user.

10. The device according to claim 1, wherein the lens includes at least one of a convex lens, a concave lens, a polarization lens, an omni-focal lens, and a color lens.

11. The device according to claim 8, the lens includes a convex lens.

12. The device according to claim 1, wherein
the lens driver includes a lead screw,
the lens is coupled to a moving body,
the moving body is coupled to the lead screw, and
the lens driver is configured to rotate the lead screw thereby causing the moving body to translate along the lead screw and cause the lens to move forward or backward.

13. The device according to claim 1, further comprising a wireless interface, wherein the controller is configured to transmit data to or receive data from an external device using the wireless interface.

14. The device according to claim 13, wherein the controller is configured to receive and store user information and exercise data using the wireless interface.

15. The device according to claim 14, wherein the controller is configured to determine the emmetropia region based on the user information.

* * * * *